(12) United States Patent
Binder et al.

(10) Patent No.: US 9,135,219 B2
(45) Date of Patent: Sep. 15, 2015

(54) METHOD AND DEVICE FOR CONTROLLING AT LEAST ONE DRIVER ASSISTANCE SYSTEM OF A VEHICLE

(75) Inventors: Hartmut Binder, Hannover (DE);
Karsten Breuer, Lauenau (DE);
Thomas Dieckmann, Pattensen (DE);
Bijan Gerami-Manesch, Burgdorf (DE); Daniel Hanslik, Isernhagen (DE);
Guido Hoffmann, Burgwedel (DE);
Heiko Kopper, Wunstorf (DE); Dirk Sandkuhler, Seelze (DE)

(73) Assignee: WABCO GmbH, Hannover (DE)

( * ) Notice: Subject to any disclaimer, the term of this patent is extended or adjusted under 35 U.S.C. 154(b) by 82 days.

(21) Appl. No.: 13/807,368

(22) PCT Filed: May 28, 2011

(86) PCT No.: PCT/DE2011/001129
§ 371 (c)(1),
(2), (4) Date: Dec. 28, 2012

(87) PCT Pub. No.: WO2012/006987
PCT Pub. Date: Jan. 19, 2012

(65) Prior Publication Data
US 2013/0103274 A1    Apr. 25, 2013

(30) Foreign Application Priority Data

Jun. 30, 2010   (DE) .......................... 10 2010 025 722
Mar. 30, 2011   (DE) .......................... 10 2011 015 509

(51) Int. Cl.
| G06F 7/00 | (2006.01) |
| G06F 17/00 | (2006.01) |
| G06F 19/00 | (2011.01) |
| B60W 40/064 | (2012.01) |

(Continued)

(52) U.S. Cl.
CPC ............. G06F 17/00 (2013.01); B60W 40/064 (2013.01); B60W 40/068 (2013.01); G01N 21/41 (2013.01)

(58) Field of Classification Search
USPC ............. 701/1, 36, 37, 45, 48, 51, 65, 70, 80; 340/901, 904, 905, 463; 356/432, 445, 356/448, 237.2; 250/339.11
See application file for complete search history.

(56) References Cited

U.S. PATENT DOCUMENTS

| 4,690,553 | A | * | 9/1987 | Fukamizu et al. ............... 356/51 |
| 5,154,268 | A |   | 10/1992 | Heuer |
| 5,163,319 | A | * | 11/1992 | Spies et al. ...................... 73/146 |

(Continued)

FOREIGN PATENT DOCUMENTS

| DE | 27 12 199 B1 | 9/1978 |
| DE | 40 03 866 A1 | 8/1991 |

(Continued)

*Primary Examiner* — Rami Khatib
(74) *Attorney, Agent, or Firm* — Kramer Levin Naftalis & Frankel LLP

(57) ABSTRACT

In a method and a device for controlling a driver assistance system of a vehicle, a process is carried out which includes the steps of emitting light of at least one wavelength onto a road surface under the vehicle, detecting the light reflected by the road surface, acquiring at least one piece of information on the nature of the road surface using the detected reflected light, transmitting the information on the nature of the road surface to the driver assistance system, and modifying at least one parameter of the driver assistance system such that the driver assistance system reacts depending on the nature of the road surface.

24 Claims, 6 Drawing Sheets

(51) Int. Cl.
*B60W 40/068* (2012.01)
*G01N 21/41* (2006.01)

(56) References Cited

U.S. PATENT DOCUMENTS

| | | | |
|---|---|---|---|
| 5,416,476 A * | 5/1995 | Rendon ........................ 340/905 |
| 5,801,647 A * | 9/1998 | Survo et al. .................. 340/905 |
| 5,962,853 A * | 10/1999 | Huth-Fehre et al. ..... 250/339.11 |
| 6,040,916 A | 3/2000 | Griesinger |
| 6,324,461 B1 * | 11/2001 | Yamaguchi et al. ............ 701/80 |
| 6,354,675 B1 * | 3/2002 | Miyazaki ...................... 303/150 |
| 6,522,968 B1 * | 2/2003 | Ito et al. .......................... 701/80 |
| 7,615,750 B2 * | 11/2009 | Dupont et al. ........... 250/339.11 |
| 8,040,248 B2 * | 10/2011 | Fridthjof .......................... 340/580 |
| 8,306,712 B2 * | 11/2012 | Deng et al. ...................... 701/65 |
| 2001/0008989 A1 * | 7/2001 | Minowa et al. ................. 701/96 |
| 2005/0004732 A1 * | 1/2005 | Berry et al. ...................... 701/48 |
| 2005/0027402 A1 * | 2/2005 | Koibuchi et al. .................. 701/1 |
| 2006/0076495 A1 * | 4/2006 | Dupont et al. ........... 250/339.11 |
| 2006/0261975 A1 * | 11/2006 | Fridthjof ....................... 340/905 |
| 2007/0016354 A1 * | 1/2007 | Engel et al. ...................... 701/80 |
| 2007/0164606 A1 * | 7/2007 | Goebels et al. ................ 303/140 |
| 2008/0129541 A1 * | 6/2008 | Lu et al. ........................ 340/905 |
| 2009/0093936 A1 * | 4/2009 | Lindgren et al. ................ 701/55 |
| 2009/0184572 A1 * | 7/2009 | Yamada et al. ................ 303/140 |
| 2010/0007200 A1 * | 1/2010 | Pelosse ............................. 303/7 |
| 2010/0141765 A1 * | 6/2010 | Capello et al. ................ 348/149 |
| 2011/0264300 A1 * | 10/2011 | Tuononen .......................... 701/1 |
| 2013/0085642 A1 * | 4/2013 | Dankers .......................... 701/48 |
| 2014/0049405 A1 * | 2/2014 | Breuer et al. ................. 340/905 |

FOREIGN PATENT DOCUMENTS

| | | |
|---|---|---|
| DE | 41 33 359 A1 | 4/1993 |
| DE | 196 47 430 A1 | 5/1998 |
| DE | 103 14 424 A1 | 10/2004 |
| DE | 10 2004 047 914 A1 | 3/2006 |
| DE | 10 2007 013 830 A1 | 10/2008 |
| DE | 10 2008 038037 A1 | 2/2010 |
| EP | 0 005 696 | 12/1979 |
| EP | 0 898 147 A2 | 2/1999 |
| EP | 1606784 | 9/2004 |

* cited by examiner

Top View

METHOD AND DEVICE FOR CONTROLLING AT LEAST ONE DRIVER ASSISTANCE SYSTEM OF A VEHICLE

FIELD OF THE INVENTION

The present invention generally relates to driver assistance systems for motor vehicles, and in particular, to a method and device for controlling such driver assistance systems.

BACKGROUND OF THE INVENTION

Nowadays, modern motor vehicles have in many cases a plurality of driver assistance systems that can assist the driver and intervene, for example, in critical situations, or in the best case help to avoid these critical situations. Such driver assistance systems comprise anti-lock brake systems (ABS), electronic stability adjusters (ESC, ESP, traction control systems), transmission controllers for automatic transmissions, shift aids, shift assistance and/or drag torque controllers (SMR, DTC), a ride level controller (ECAS) and/or an offroad mode, and can also include other systems.

Some driver assistance systems such as ABS or ESC, ESP and traction control systems have speed sensors on each wheel in order to detect automatically the speed at which each wheel is rotating. If differences are detected here, this can indicate a slippery roadway with a low coefficient of friction. These systems are usually based on the principle of measuring the rotational speed of the vehicle wheels. The speed sensors may be of purely mechanical design, but they usually now operate with inductive sensors or Hall sensors in a contact-free fashion. The speed sensors can be mounted on each wheel, such as is customary, for example, in ABS systems. However, these systems have the disadvantage that they cannot detect a low coefficient of friction and therefore a potentially dangerous situation until differences in wheel speed are detected, that is when the vehicle is already skidding.

Other driver assistance systems such as SMR or automatic transmissions generally do not have any information whatsoever about the state of the roadway, with the result that, for example when shifting into a relatively low gear speed, critical driving states can be caused by the engine braking torque.

SUMMARY OF THE INVENTION

Generally speaking, it is an object of the present invention to overcome the disadvantages described above by means of a method and device for controlling at least one driver assistance system of a vehicle.

According to one aspect of the invention, the method comprises emitting light of at least one wavelength onto a roadway surface under the vehicle, detecting light of the at least one wavelength reflected at the roadway surface, acquiring at least one information item relating to the condition of the roadway surface on the basis of the detected reflected light of the at least one wavelength, transmitting the at least one information item relating to the condition of the roadway surface to the at least one driver assistance system, and changing at least one parameter of the at least one driver assistance system, with the result that the at least one driver assistance system acts as a function of the condition of the roadway surface.

According to another aspect of the invention, the device comprises an optical surface sensor for acquiring at least one information item relating to the condition of a roadway surface, and a controller that is connected to the optical surface sensor and to the at least one driver assistance system, and that changes at least one parameter of the at least one driver assistance system on the basis of the at least one information item relating to the roadway surface, with the result that the at least one driver assistance system acts as a function of the condition of the roadway surface.

With the method and the device, the driver assistance system can be adapted to the roadway situation before the driver assistance system detects an unsafe state of the roadway. The driver assistance system can therefore act more quickly and avoid critical driving situations before they even occur.

In one embodiment, the optical surface sensor can sense whether the roadway surface is dry, wet, icy or snow covered. It can also determine the thickness of a film of water or a layer of ice on the roadway surface. The optical surface sensor can also sense the roughness of the roadway surface in order to detect whether the roadway surface is asphalt, concrete or a relatively rough underlying surface, with the result that an offroad situation can be determined. This information about the condition of the roadway surface can be made available to the driver assistance system.

In a further embodiment, the driver assistance system can comprise an anti-lock brake system (ABS). The information relating to the condition of the roadway surface can be used to set a first control cycle of the anti-lock brake system as a function of the condition of the roadway surface. It is therefore possible, for example, to provide for a smaller degree of braking in the first control cycle if a wet roadway surface has been determined, in order to prevent excessive overbraking of the ABS. The braking can be reduced further if the vehicle is located on a slippery underlying surface such as ice or snow. The customary first control cycle with strong braking can therefore be replaced by a presetting, with the result that the brake pressure is adapted more quickly.

In another embodiment, the driver assistance system can also comprise a traction control system in which at least the first control cycle is also adapted as a function of the condition of the roadway surface.

In still a further embodiment, the driver assistance system can comprise a stability adjuster (ESP, ESR). Intervention, for example a time of intervention or some other parameter of the intervention, by the stability adjuster can be adapted to the determined condition of the roadway.

For example, it is possible to provide for a steering wheel lock, the vehicle speed and, if appropriate, further parameters to be adjusted to the determined condition of the roadway surface, and to determine whether the lateral forces which are calculated in advance for the determined condition of the roadway surface make it necessary to intervene in the stability adjuster. It is therefore possible to achieve early intervention by a stability adjuster, the intervention being adapted to the current condition of the roadway.

The driver assistance system can comprise a transmission controller for an automatic transmission. An automatic transmission may comprise any type of automated gear speed change.

It is possible to provide, for example, for the shift characteristic to be adapted to the determined condition of the roadway surface. For example, in wintery roadway conditions with a low coefficient of friction, when, for example, snow or ice has been determined on the roadway, it is possible to provide for starting up in a relatively high gear speed, for example in the second or third gear speed, in order to prevent spinning of the driven wheels. Relatively early shifting in roadway conditions with a low coefficient of friction can also be provided.

It is also possible to provide, in particular in vehicles with a drag torque controller, for early shifting in a relatively low gear speed to be prevented if the vehicle is located on a roadway surface with a low coefficient of friction. In this way, it is possible to avoid a situation in which the intervention by the engine brake causes the vehicle to skid or enter some other critical state. A maximum transmissible drag torque can be determined by using the determined condition of the roadway surface and the coefficient of friction acquired therefrom and, if appropriate, further vehicle parameters such as velocity, state of the tires and the like. If the expected drag torque cannot be transmitted when shifting down occurs, it is possible to provide for the shifting time to be moved or to be counteracted by means of a drag torque controller or DTC function, for example by briefly opening the throttle.

In one embodiment, the driver assistance system can also comprise an offroad mode. It is possible to provide the vehicle to be switched to an offroad mode, if the information relating to the condition of the roadway surface indicates that the vehicle is not on a metalled road with a low degree of roughness, such as asphalt or concrete. It is possible for the offroad mode to be activated automatically in such a case. The offroad mode may comprise, for example, the switching on of an all-wheel drive or of some other traction aid. The offroad mode can also comprise the setting of a ride level adaptation device in order to increase, for example, the ground clearance of the vehicle.

If the optical surface sensor detects that the vehicle is located again on a metalled roadway, the offroad mode can be correspondingly switched off automatically.

In particular, in the case of ABS and stability adjusters, and also in other driver assistance systems, it is possible to provide in each case an optical surface sensor in front of each wheel of the vehicle so that the condition of the roadway surface for each wheel can occur individually and the intervention of the driver assistance system can be correspondingly set.

According to an embodiment, the optical surface sensor can comprise a light source unit for emitting light of at least one wavelength onto the underlying surface and at least one detector for detecting light reflected by the underlying surface.

In a further embodiment, the surface sensor can comprise a second detector in addition to the first detector, wherein the first detector is suitable for sensing diffusely reflected light and the second detector is suitable for sensing light reflected in a mirroring fashion. At least two polarizers can be provided, wherein a first polarizer with a first polarization device is assigned to the first detector. The light source unit can be assigned a light source polarizer and/or the second detector can be assigned a second polarizer whose polarization device or devices is/are oriented substantially perpendicularly with respect to the first polarization direction of the first polarizer. If at least two polarizers or polarization filters are provided, the first polarizer is arranged on the first detector, which transmits only light waves in the first polarization direction to the first detector. If a light source polarizer is provided on the light source unit, the polarization direction thereof is arranged substantially perpendicularly with respect to the first polarization direction of the first polarizer, and the light emitted by the sensor is polarized in a direction substantially perpendicular with respect to the first polarization direction. In this way, the light that is polarized at the first detector and reflected in a mirroring fashion is filtered out and only diffusely reflected light is detected. A similar effect can be achieved when a second polarizer is arranged in front of the second detector, the polarization direction of which second polarizer is oriented substantially perpendicularly with respect to the first polarization direction. The second polarizer can be used as an alternative to or in addition to the light source polarizer. It is also possible to provide for light that is already polarized to be generated in the light source unit.

In a still further embodiment, the light source unit can be configured to emit light of at least two different wavelengths onto the underlying surface or the roadway surface. For this purpose, the light source unit can comprise, for example, a plurality of light sources. The use of at least two, preferably three different wavelengths makes it possible to operate the sensor in a spectral fashion. Using wavelengths which can be particularly well absorbed by, for example, ice or water, allows ice or water to be detected on the roadway or the roadway surface if the reflected light of the wavelength that is absorbed by the water or the ice is compared with that of a reference wavelength. It is therefore possible to implement the principles of spectral analysis and of diffuse reflection and mirroring reflection in just one device or in a single housing. The at least one light source unit, the first detector and, if appropriate, the second detector can for this purpose be arranged in a common single and/or one-piece housing, for example directly one next to the other.

It is possible to use light in at least three different wavelengths in the infrared range. The light source unit can for this purpose comprise a plurality of light sources. For example, the light source unit can be configured to emit infrared light at the wavelengths 1300 nm, 1460 nm and 1550 nm. While light of the wavelength 1460 nm is particularly well absorbed by water, light of the wavelength 1550 nm is well absorbed by ice. Light in the region of approximately 1300 nm can then be used as a reference wavelength. However, other wavelengths can also be used, in particular for the reference wavelength, it is possible to use any other wavelength that is not appreciably absorbed either by ice or water. Any other wavelength that is absorbed to an increased degree in water can also be used as a water-sensitive wavelength. Any wavelength that is absorbed to an increased degree in ice can equally be selected as an ice-sensitive wavelength. Other wavelengths of interest include, for example, 1190, 1040, 970, 880 and 810 nm in the infrared range, as well as the visible wavelengths 625, 530 and 470 nm.

In another embodiment, the light source unit can be configured to emit light of precisely three different wavelengths. For this purpose, the light source unit can have three light sources, one light source for each wavelength. Only the three wavelengths are used in order to sense light that is reflected in a spectral as well as mirroring/diffuse fashion so as to determine or detect both the condition of the roadway and the type of the roadway. Any of the light sources can be actuated individually and be switched on and off independently of the others or can be adjusted in intensity.

Furthermore, it is also possible to use more than the above-mentioned two or three different wavelengths. For example, the wavelength 625 nm can also be used to measure the light reflected in a diffuse and mirroring fashion.

It is also possible to provide for the emitted light to be modulated in intensity and/or amplitude. The modulation of the intensity or amplitude can be carried out by switching all the light sources or individual light sources of the light source unit on and off. The modulation of the intensity or the switching on and off can take place separately for each wavelength of the light source unit or for each light source of the light source unit. The modulation of the amplitude or intensity or the switching on and off for each wavelength can, for example, take place with the same frequency but in a phase-shifted fashion and/or with different frequencies. As a result, it is possible to cause, for example, the light of different wavelengths to be emitted in a chronologically offset fashion or sequentially. For example, it is possible to provide for light of a first wavelength to be emitted for a specific time interval and for the light of the first wavelength to be switched off and for a second wavelength to be switched on, etc. Light from just one wavelength is then respectively detected in the detectors. As a result, a spectral analysis or splitting of the incident light on the detectors can be avoided. Mixed forms of various modulation techniques can also be applied, in particular frequency-modulated and amplitude-modulated optical signal traces with or without interruptions.

Simple detectors can be used as a first or second detector. For example, the first detector and the second detector can each comprise one or more photodiodes. At least the first detector can be configured to sense light of all the wavelengths that are emitted by the light source unit. The detector can also alternatively or additionally comprise an opto-electronic chip (for example CCD) or some other optical recording device.

The first and second detector can be used to sense or determine light that is reflected in a mirroring fashion and diffusely reflected light. In addition, at least one of the first and second detectors can also be used for the spectral determination. At least this detector is configured to detect light of a plurality of wavelengths. In this example, the sensor includes the first detector and the second detector, and no further detectors are provided.

According to another embodiment, surface sensor can also comprise an evaluation device that outputs information about the condition of the roadway surface or of the underlying surface.

Still other objects and advantages of the present invention will in part be obvious and will in part be apparent from the specification.

The present invention accordingly comprises the several steps and the relation of one or more of such steps with respect to each of the others, and embodies features of construction, combinations of elements, and arrangement of parts adapted to effect such steps, all as exemplified in the detailed disclosure hereinafter set forth, and the scope of the invention will be indicated in the claims.

BRIEF DESCRIPTION OF THE DRAWINGS

Further details and examples of embodiments of the invention are discussed in greater detail below with reference to the appended drawings, in which.

DETAILED DESCRIPTION OF THE PREFERRED EMBODIMENTS

Figure 1A:
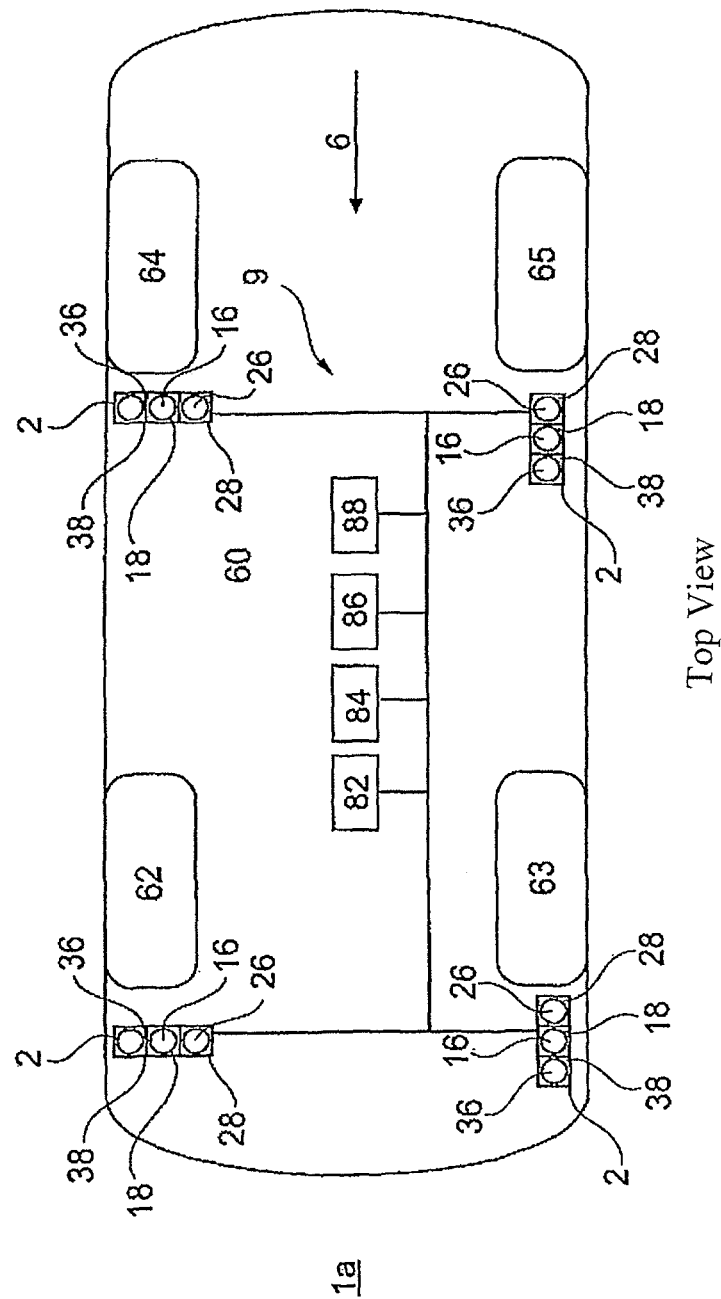
FIGS. 1a and 1b show plan and side views of a device in a vehicle according to an embodiment of the invention.

FIG. 1a shows a vehicle 60 which is equipped with examples of a device 9 according to an embodiment of the invention.

The vehicle 60 comprises a surface sensor 2 in front of each wheel, in particular a surface sensor 2 in front of the right-hand front wheel 62, a surface sensor 2 in front of the left-hand front wheel 63, a surface sensor 2 in front of the right-hand rear wheel 64 and a surface sensor 2 in front of the left-hand rear wheel 65, wherein the designations in front of, behind, right-hand and left-hand relate to the normal direction of travel 6 of the vehicle. The surface sensor 2 is respectively arranged in front of the corresponding wheel, in the track thereof. The sensor 2 is arranged in such a way that a light emitter opening 18 with an emitter optics 16, a first detector opening 28 with a first collector optics 26 and a second detector opening 38 with a second collector optics 36 can be seen from the carriageway 1. As illustrated, a sensor 2 is arranged in front of the right-hand front wheel 62 and another sensor 2 is arranged in front of the right-hand rear wheel 64, substantially in a row transversely with respect to the direction of travel of the vehicle. A sensor 2 is likewise arranged in front of the left-hand front wheel 63 and yet another sensor 2 is arranged in front of the left-hand rear wheel 65 in the direction of travel that is characterized by an arrow 6. The orientation of the sensors is merely exemplary and all the sensors may be oriented in the same way.

As illustrated, the vehicle 60 has four wheels, though, it is possible to provide more wheels. The vehicle can be a passenger car, a utility vehicle or some other type of vehicle.

Each of the sensors 2 in the example illustrated in FIG. 1 is connected to a controller of the driver assistance systems which comprise the controller of an anti-lock brake system 82, the controller of a stability adjuster 84, a transmission controller 86 and an offroad mode controller 88. In addition to the illustrated driver assistance systems, further driver assistance systems can be connected to the sensors 2. It is also possible to provide for just one, or for a selection, of the driver assistance system to be connected to the sensors 2. The driver assistance systems can be systems which are already known and provided in the vehicle and correspondingly adapted or provided specially for the connection to the sensors 2.

Figure 1B:
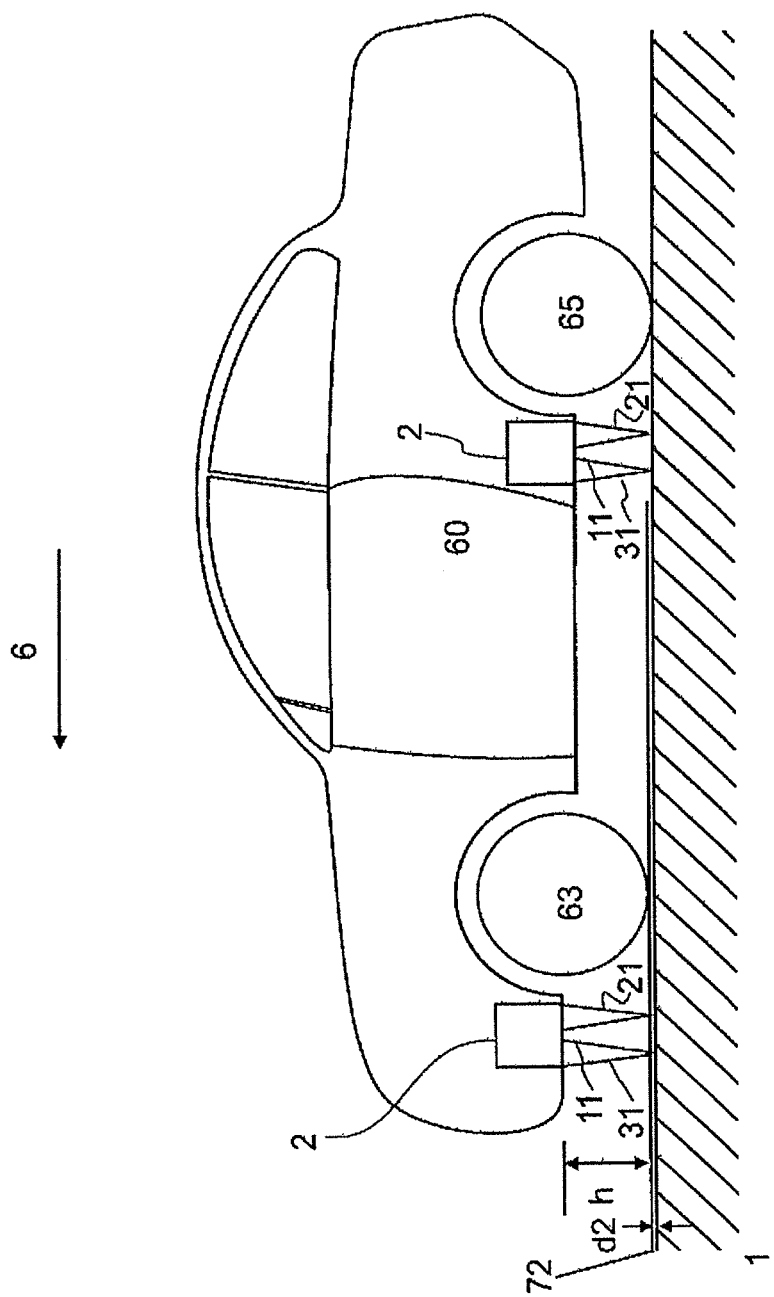

FIG. 1b shows the vehicle 60 in a side view. The vehicle is located with the left-hand front wheel 63 on a single layer 72 with the thickness d2, while the left-hand rear wheel 65 is located on a dry roadway surface 1a.

Figure 2:
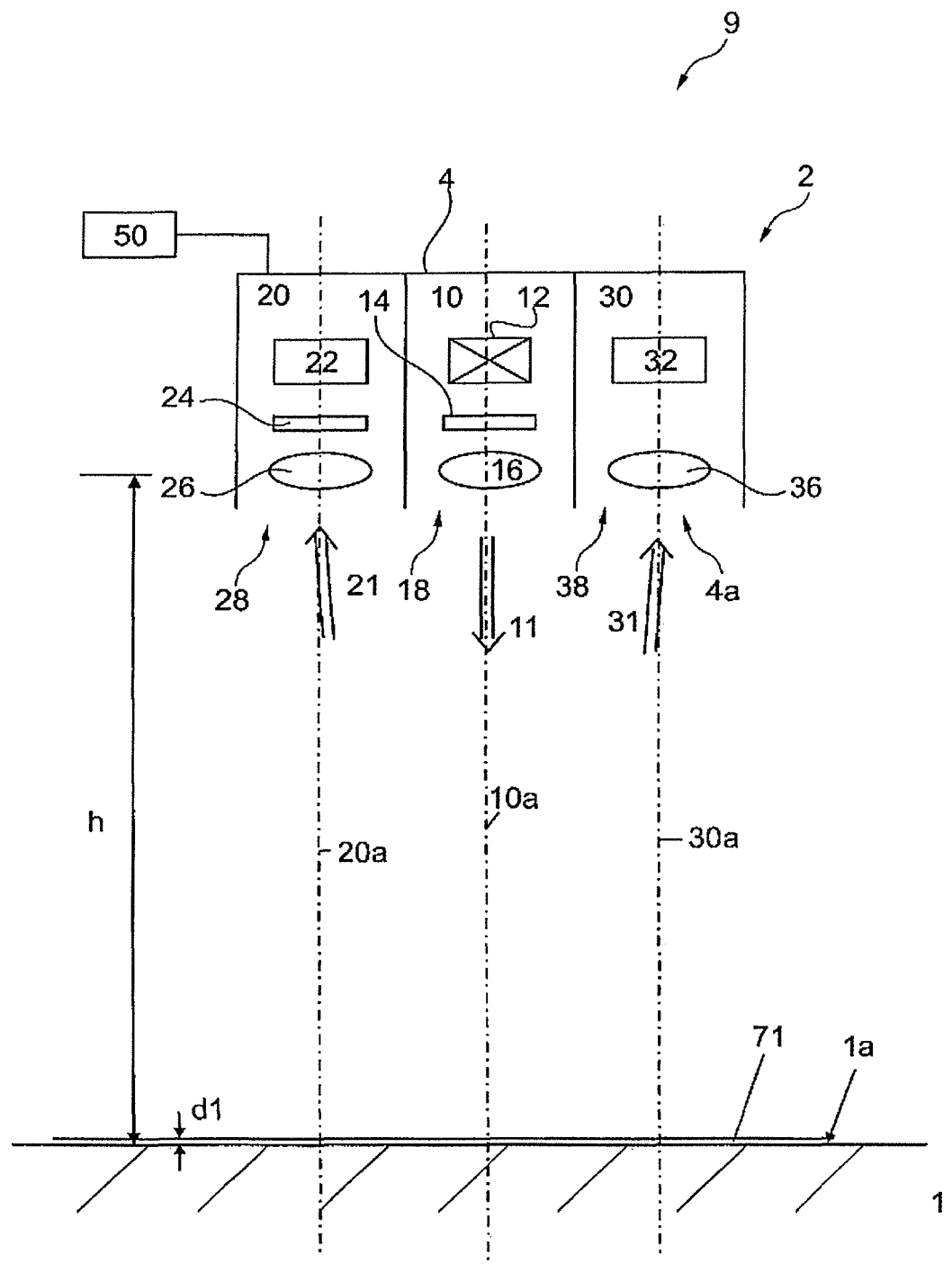
FIG. 2 shows a first example of a device according to an embodiment of the invention.
Figure 3:
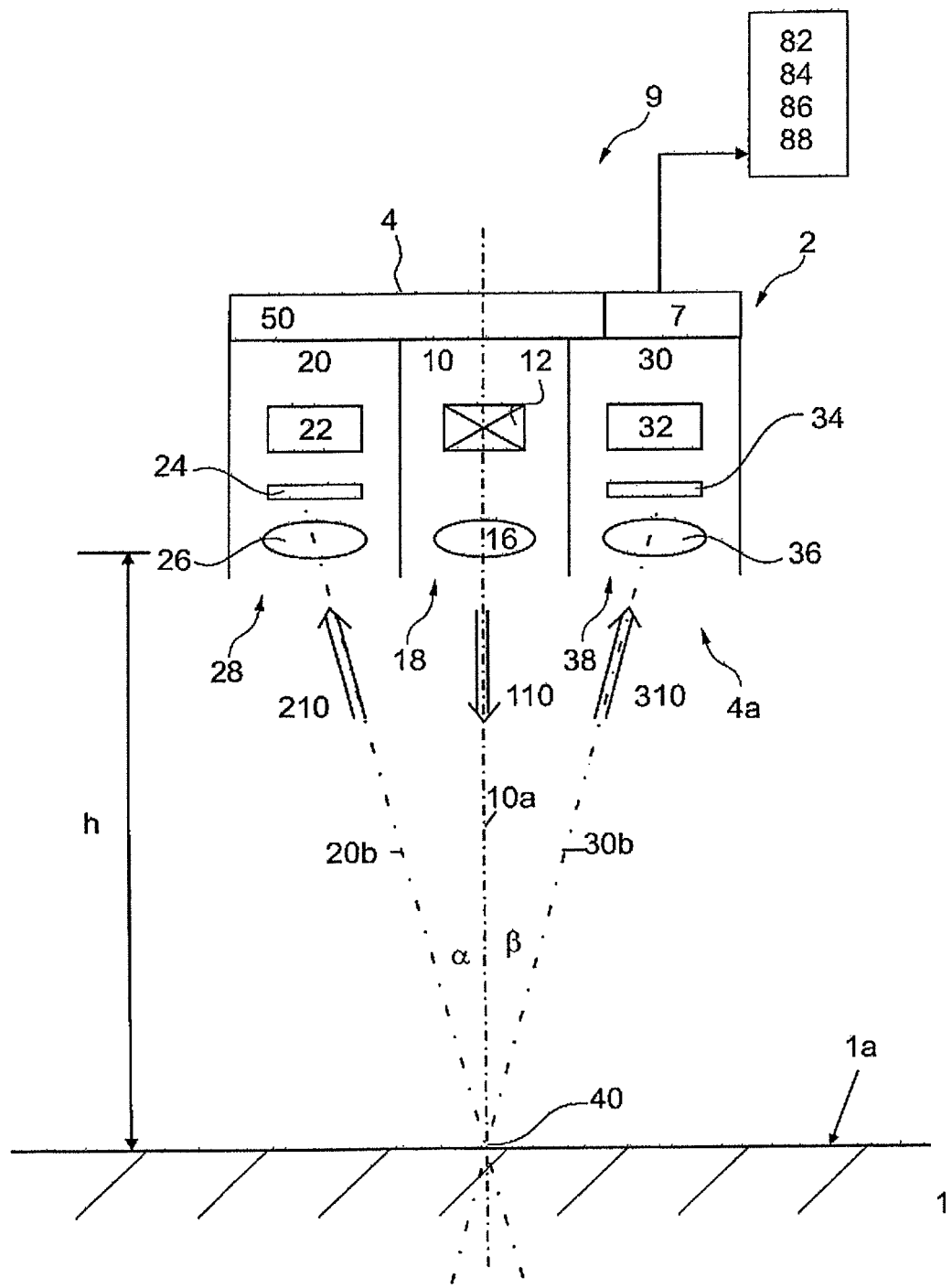
FIG. 3 shows a second example of a device according to an embodiment of the invention.

An example of one of the sensors 2 is illustrated in detail in FIGS. 2 and 3.

The surface sensor 2, also denoted here as sensor 2 for detecting the condition, in particular a state, and the type of the surface of a roadway 1 or roadway surface 1a, is configured to be mounted on a motor vehicle 60.

The sensor 2 comprises, in a housing 4, three devices, including a light emitter device 10, a first detector device 20 and a second detector device 30. The light emitter device 10 has a light emitter window or a light emitter opening 18 in the housing, the first detector device 20 has a first detector window or a first detector opening 28 in the housing, and the second detector device 30 has a second detector window or a second detector opening 38 in the housing. The light emitter opening 18, the first detector opening 28 and the second detector opening 38 are arranged on the same side 4a of the housing and oriented towards the roadway 1 when the sensor 2 is mounted in an operationally ready fashion on the vehicle. The sensor 2 is oriented such that the emitted light beam 11 is incident approximately perpendicularly on the roadway 1 or roadway surface 1a (i.e., the optical axis of the light emitter section 10a or the light emitter axis 11a is substantially perpendicular with respect to the roadway 1 or roadway surface 1a). In the illustrated example, a film 71 of water with the thickness d1 is located on the roadway surface 1a. However, the roadway surface can also be snow covered, icy or dry or can have some other condition.

In the examples illustrated in FIGS. 2 and 3, the light emitter device 10, the first detector device 20 and the second detector device 30 are arranged in a row, and the light emitter device 10 is arranged between the first detector device 20 and the second detector device 30.

The light emitter device 10, the first detector device 20 and the second detector device 30 can, however, also be arranged separately from one another and do not have to be combined in one housing.

A light source unit 12, that is configured to emit light of a plurality of different wavelengths, is arranged in the light emitter device 10. The light source unit 12 can for this purpose comprise one or more light-emitting diodes (LEDs), laser diodes or some other light source or a combination thereof that is suitable for emitting light of a plurality of different wavelengths. For example, the light source unit 12 can emit light at least in the wavelengths 1300 nm, 1460 nm and 1550 nm. However, the wavelengths which are provided can be adapted to the respective purpose of use.

In the example illustrated in FIG. 2, a light source polarizer or light source polarization filter 14 is connected downstream of the light source unit 12 in the direction of the emitted light beam 11, which light source polarizer or light source polarization filter 14 polarizes the light in a predetermined direction, and which light is emitted by the light source unit 12.

In addition, emitter optics 16 are provided for orienting or focusing the emitted light along an emitted light beam 11 onto a specific region on the underlying surface or the roadway 1 or the roadway surface 1a under the vehicle 60. The optical axis of the emitter optics 16 can define the optical axis 10a of the light emitter section 10. The emitter optics 16 can be composed of an emitter lens or of a plurality of lenses and/or comprise another optical element.

The first detector section 20 comprises a first detector 22, for example one or more photodiodes, configured to detect light of all the wavelengths emitted by the light source unit 10. The first detector 22 can for this purpose also comprise a plurality of photodiodes which are arranged one next to the other, or one or more opto-electronic units (for example CCD, CMOS).

A first collector optics 26 and a first polarizer or first polarization filter 24 are arranged on the first detector 22. The first collector optics 26 can be composed of an individual first collector lens or can comprise a plurality of lenses and/or further optical elements. The polarization direction of the first polarization filter 24 is perpendicular with respect to that of the light source polarization filter 14 and is therefore substantially perpendicular with respect to the predetermined polarization direction. Light that is reflected in a mirroring fashion and is polarized in the predetermined direction is therefore filtered out and only diffusely reflected light passes to the first detector 22. The first detector 22 therefore serves as a "scattering detector".

A first axis 20a can correspond substantially to the optical axis of the first collector optics 26 and/or of the first detector section 20 and can be oriented substantially parallel to the emitter axis 10a, which corresponds substantially to the optical axis of the emitter optics 16 and/or of the light emitter section 10.

A second detector 32 is arranged in the second detector section 30, which, in turn, is arranged on the side of the light emitter section 10 lying opposite the first detector section 20, in the housing 4 of the sensor 2.

The second detector 32 can also comprise a photodiode configured at least to detect light of one wavelength emitted by the light source unit 12. However, the second detector 32 can also comprise a plurality of photodiodes arranged one next to the other and configured to detect light of a plurality of different wavelengths or wavelength ranges.

The second detector 32 is assigned a second collector optics 36 in order to focus the reflected light onto the second detector 32 and detect it therein. The second collector optics 36 can be composed of an individual, second collector lens or comprise a plurality of lenses and/or further optical elements. In contrast to the first detector 22, the second detector 32 in the example illustrated in FIG. 1 does not have a polarizer or polarization filter. Since the emitted light is already polarized, this is not necessary. Diffusely reflected light and light reflected in a mirroring fashion is detected by the second detector, the light being reflected along the second detector beam path 31. However, the second detector 32 can also have a polarization filter (not illustrated) whose polarization direction is parallel to that of the emitter polarizer 16, in order to detect in the second photodiode 36 only light that is reflected in a mirroring fashion.

A second axis 30a can correspond substantially to the optical axis of the second collector optics 36 and/or of the second detector section 30 and be oriented substantially parallel to the emitter axis 10a, which corresponds substantially to the optical axis of the emitter optics 16 and/or of the light emitter section 10.

The sensor described can be operated in the visible light range, for example at a wavelength of approximately 625 nm, in order to measure light reflected in a mirroring fashion and diffusely reflected light. From the ratio of the diffusely reflected light measured in the first detector 22 to the light reflected in a mirroring fashion and additionally measured in the second detector 32, it is possible to infer the brightness of the roadway and the roughness of the roadway, and therefore determine whether the vehicle is located, for example, on an asphalt roadway or concrete roadway.

The described sensor can also be used at various wavelengths in the infrared range. For this purpose, the first detector 22 and/or the second detector 32 can be used. For example, infrared light of the wavelength 1460 nm is particularly well absorbed so that, in the case of a wet roadway, light of this wavelength is reflected back to the first detector 22 or to the second detector 32 only to a small degree, whereas, in the case of a dry roadway, this wavelength is reflected normally. In contrast, infrared light of the wavelength 1550 nm is well absorbed by ice. By comparing the reflection of these two wavelengths and taking into account a reference wavelength it is possible to infer that there is ice or water on the roadway. The reference wavelength that is not appreciably absorbed either by ice or water, for example 1300 nm, serves as a reference variable for the evaluation of the degree of absorption of the two other wavelengths. The measured intensity ratio at the wavelengths 1550 nm/1300 nm can then be placed in relationship with the ratio 1460 nm/1300 nm in a known fashion in order to obtain information about the water and ice on the roadway or a dry roadway.

The various wavelengths can be emitted in parallel, and, in particular, sequentially with a chronological offset. It is therefore respectively possible to emit only light of one wavelength at a time and correspondingly detect it. This makes it possible to dispense with complex spectral analysis or splitting of beams.

The sensor 2 also has an evaluation device 50 with which the data which are detected or determined by the first detector 22 and the second detector 32 are processed. The evaluation device 50 can be arranged outside the housing 4 and be located, for example, at another location in the vehicle 60. The evaluation device 50 can be connected to the first detector 22 and the second detector 32 via a cable or a wireless connection. The evaluation device can also comprise a controller for the light source unit 21 or be connected to a controller. The evaluation unit 50 and/or the controller can, however, also be arranged on or in the housing 4 or integrated therein, as illustrated in FIG. 2.

With the described sensor 2, it is possible to measure both spectral reflection and mirroring and diffuse reflection in a short time sequence with a compact and cost-effective design, and on this basis infer the type of roadway and the state of the roadway. As a result, better and more precise information is provided about the type and the actual state of the roadway 1 or roadway surface 1a under the vehicle 60. Just the one sensor 2 is necessary for the measurement.

If the spectral reflection is to be measured, since, for example, the measuring accuracy is sufficient for this, the second detector section 30 can, if appropriate, be omitted.

FIG. 3 shows a further example of a device 9. The features which are illustrated and described with respect to FIG. 3 can be combined or replaced depending on the application with the features which are illustrated and described with respect to FIG. 2.

The sensor 2 illustrated in FIG. 3 corresponds to the sensor described with respect to FIG. 2, with the difference that no light source polarizer is provided. The emitted light beam 110 is not polarized in this case. In order, nevertheless, to be able to filter out light that is reflected in a mirroring fashion, a second polarization filter 34 is arranged in front of the second detector 32 in the beam path. The polarization direction of the second polarization filter 34 is substantially perpendicular with respect to the polarization direction of the first polarization filter 24. All the other elements of the sensor 2 can correspond to those of the sensor illustrated with respect to FIG. 2.

In the example illustrated in FIG. 3, there is neither a film 71 of water nor a layer 72 of ice on the roadway surface 1a.

In the example illustrated in FIG. 3, the first axis 20b, which can correspond to the optical axis of the first collector optics 26 and/or of the entire first detector section 20, is oriented at an angle α with respect to the emitter axis 10a, wherein the angle α is at most approximately 10°. Correspondingly, the second axis 30b, which can correspond to the optical axis of the second collector optics 36 and/or of the entire second detector section 30, can be oriented at an angle β with respect to the emitter axis 10a, wherein the angle β is likewise at most approximately 10°. The point 40 of intersection of the emitter axis 10a with the first axis 20b and/or the second axis 30b can lie on the roadway surface 1a or at a distance of up to 50 cm from the roadway surface 1a.

There is also the possibility of providing both the light source polarizer or light source polarization filter 14 on the light source unit 12, as described with respect to FIG. 2, as well as a second polarizer or second polarization filter 34 on the second detector 32. The polarization directions of the light source polarization filter 14 and the second polarization filter 34 are then typically oriented parallel to one another. The polarization directions of the light source polarization filter 14 and of the second polarization filter 34 of the second detector 32 are, however, arranged substantially perpendicularly with respect to the polarization direction of the first polarizer or of the first polarization filter 24.

In addition, as illustrated in FIG. 3, the evaluation device 50 is arranged inside the housing 4 of the sensor 2 and integrated into the housing. Of course, the evaluation unit can also be provided outside the sensor 2, as is illustrated in FIG. 2.

The sensor 2 and, in particular, the emitter optics 16 and the first collector optics 26 or, if appropriate, also the second collector optics 36 can be arranged at a specific height or a specific height region above the roadway surface 1a. For example, the sensor 2 can be arranged at a height h or a distance of approximately 10 cm to 1 m from the roadway surface 1a, wherein the distance can be adapted a respective purpose of use. For the use of the sensor 2 in a passenger car, the height h can be in the range from approximately 10 cm to 40 cm. When the sensor 2 is used in a utility vehicle, a bus or an offroad vehicle, the height h can be approximately 30 cm to 100 cm, in particular in a range from 50 cm to 80 cm.

Figure 4:
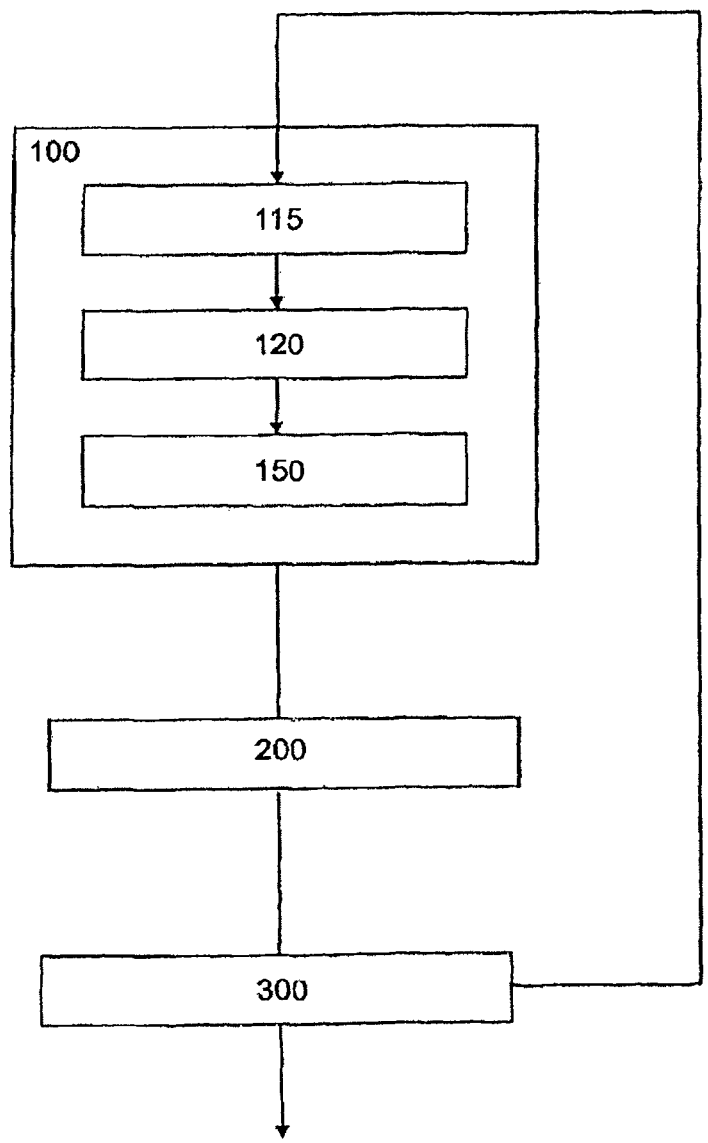
FIG. 4 illustrates a method according to an embodiment of the invention.

FIG. 4 shows by way of example a method for controlling a driver assistance system. The method comprises the step 100 of collecting information relating to a condition of the roadway or the condition of a roadway surface 1a. The collecting of the information relating to the condition of the roadway surface 1a comprises a step 115 of emitting light of at least one wavelength, preferably of at least three different wavelengths in the infrared range, and a step 120 of detecting light reflected at the roadway surface 1a. As described above, the light of the different wavelengths can be emitted in a chronologically offset fashion, for example modulated with a different frequency or modulated in a phase-shifted fashion with the same frequency and correspondingly detected. This makes it possible to use just one detector for a plurality of wavelengths and, if appropriate, the background radiation in the case of switched-off light sources.

Information about the condition of the roadway surface 1a is then acquired in step 150 from the ratio of the light intensities of the reflected light of the different wavelengths or from the ratio between the diffusely reflected light and the light reflected in a mirroring fashion, that is, whether the roadway 1a is dry, wet, icy, snow covered or is in some other condition. In this step, the thickness d1 of a film of 71 water or the thickness of a layer 72 of ice on the roadway surface 1a can also be determined.

If the condition of the roadway surface 1a has been detected, in step 200, this information is transmitted to the driver assistance system and it is determined, if appropriate by adding further parameters such as the vehicle speed, a lateral acceleration, a transmission rotational speed, how the driver assistance system is to be influenced and which parameter or parameters of the driver assistance system is/are to be changed. In step 300, a corresponding parameter of the driver assistance system is then changed.

Figure 5:
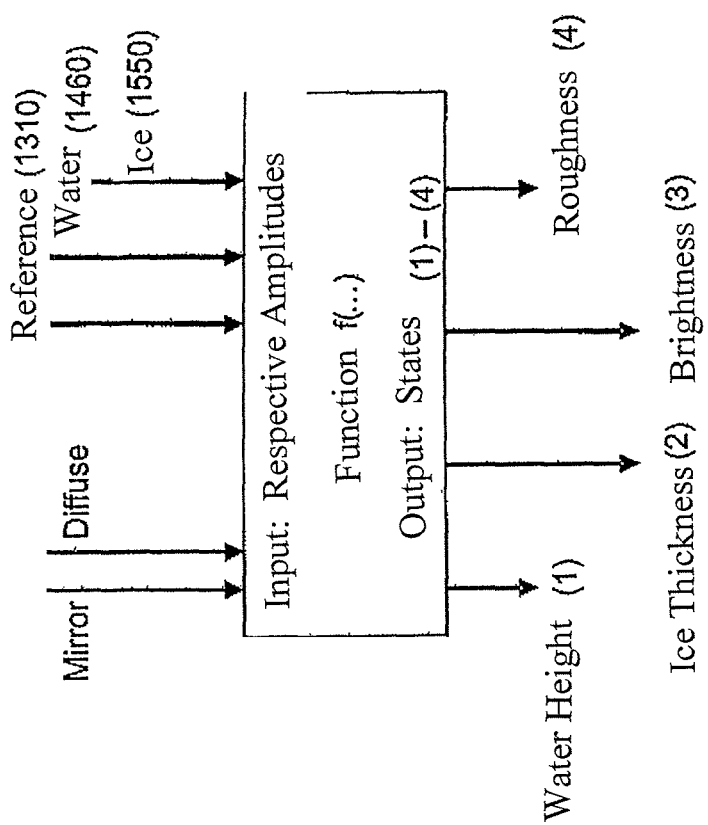
FIG. 5 shows an exemplary evaluation of light intensities according to an embodiment of the invention.

The determination of the roadway condition is illustrated basically in FIG. 5. The roadway conditions of the height of water d1 on the roadway surface 1a, the thickness d2 of the ice on the roadway surface 1a, a value for the brightness d3 and/or for the roughness d4 of the roadway surface 1a are determined from the acquired light intensities for diffusely reflected light and for light reflected in a mirroring fashion as well as of the diffusely reflected light of the above-mentioned different wavelengths in the infrared range.

If no thickness d2 of the ice and no height d1 of the water has been determined, but an increased level of roughness has been detected, it is possible to conclude therefrom that the vehicle 60 is not located on a metalled roadway 1 and an offroad mode 88 has been switched on. The activation of the offroad mode 88 can comprise switching on of an all-wheel drive, the switching on of mechanical and/or electronic differential locks, the setting of the ride level of a ride level control system and/or the adaptation of a control threshold of the ABS.

If a specific thickness d1 of a film 71 of water, a specific thickness d2 of a layer 72 of ice and/or a dry roadway surface 1a are determined, this information can be made available, for example, to the controller of the ABS 82. The control cycle can then be adapted individually for each wheel. Depending on the roadway condition, a coefficient of friction for the driving situation can then be estimated, and the first control cycle of the ABS can be set such that overbraking, and therefore relatively long blocking of a wheel can be prevented. As a result, the adjustment of the ABS during a braking process takes place more quickly.

If appropriate, further variables can be included in the determination of the braking force, such as the height of the center of gravity in a laden/unladen vehicle.

The determination of the braking force at the respective wheel can be carried out, for example, with the formula $$F_{setp} = \mu_{max} p(G + AG) c,$$

wherein the $F_{setp}$ is the braking force, $\mu_{max}$ is the coefficient of friction determined by means of the sensor 2, p is the brake pressure, G is the static axle load, AG is a dynamic axle load and c is a factor. The objective here is to achieve an equilibrium between the braking force at the respective wheel and the brake pressure.

A traction control system can also be actuated in a way analogous to the control of an ABS 82, and the driving or braking of a wheel can respectively take place as a function of a currently determined coefficient of friction.

In order to control a stability controller 84 such as an ESC or ESP, the current coefficient of friction determined at each wheel by means of the sensor 2 can be compared with a necessary coefficient of friction. The necessary coefficient of friction can be determined, for example, from the velocity and the steering wheel lock for cornering and, if appropriate, further variables.

The coefficients of friction for determining the necessary coefficient of friction are obtained, on the one hand, from the vectorial addition of the longitudinal forces (driving & braking) and of the side forces. The longitudinal forces can be calculated from the engine torque and the brake pressures with a good approximation. The side forces can be obtained in a first approximation from the single-track model of the ESC controller. During all the driving maneuvers in which the vehicle does not travel straight ahead, it moves on a circular path. This circular path is described by the quasi-steady-state lateral acceleration forces which are measured directly in the ESC module, and by dynamic components which can be determined on the basis of the respectively measured lateral acceleration. Given knowledge of the geometry of the vehicle, the necessary yaw guidance forces can then be calculated for the front wheels 62,63 and the rear wheels 64,65. In addition, by changing over from the single-track model to the real two-track model, it is possible to distribute these forces between the left and right-hand sides given peripheral assumptions.

In this way, an estimate of the frictional forces that are instantaneously present at each wheel is obtained. If the adhesion limit, determined by a sensor 2, is approached, for example during accelerated circular-course driving, stabilizing measures can already be taken before instability occurs. In other words, if the necessary coefficient of friction approaches the determined current coefficient of friction or becomes smaller, premature intervention by the stability controller 84 can take place.

The information about the condition of the roadway can also be used to determine a maximum possible drag torque.

The forces which occur at the tire as a result of shifting down can be calculated or estimated in the following way: the transmission ratio of the transmission 87 is known or can be calculated from the ratio, which can be determined for each gear speed, between the engine speed and the velocity. A quasi-steady-state component of frictional torque can be specified (as a function of the rotational speed) for each engine, together with a dynamic component which results from the moment of inertia of the engine and the necessary acceleration (or change in rotational speed).

The force on the tire that is necessary to overcome the frictional torque and accelerate the engine to the target rotational speed can be calculated for the purpose of shifting down into a particular gear speed. If this drive force is then divided by the wheel load that is present (which can be derived from the control of the differential slip), the necessary required coefficient of friction is obtained. If this necessary coefficient of friction is then compared with the coefficients of friction determined at a particular time at the driven wheels by means of the sensor 2, it is already possible, when there is an intention to shift, to determine whether the wheels will slip and therefore cause a state that is critical for stability to arise. The shifting down can already be prevented in advance, or the engine can be speeded up to the target rotational speed. For this purpose, DTC or SMR systems which are known per se can be used.

The preceding description was produced with respect to the examples illustrated in the figures. However, a person skilled in the art can readily modify or combine the specified examples and supplement them with, for example, warning signals or further control signals and further driver assistance systems. A person skilled in the art will also find further application possibilities of the device and the method, for example mounting at other locations on a vehicle.

A person skilled in the art will also consider other wavelengths than those specified in order to adapt the measurement results to different requirements. Of course, the specified wavelengths are not restricted to the values precisely but rather can comprise a wavelength range which contains the specified discrete wavelengths.

It is also possible to supply not only one but also a plurality or all of the driver assistance systems 82, 84, 86, 88 of a vehicle with the information about the condition of the roadway surface 1a, in order to change at least one parameter of the respective driver assistance system 82, 84, 86, 88 as a function of the condition of the roadway surface 1a.

It will be seen that the objects set forth above, among those made apparent from the preceding description, are efficiently attained, and since certain changes may be made without departing from the spirit and scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described and all statements of the scope of the invention that, as a matter of language, might be said to fall therebetween.

What is claimed is:

1. A method for controlling at least one driver assistance system of a vehicle, the at least one driver assistance system comprising a stability adjuster, the method comprising:
    emitting light of at least one wavelength onto a roadway surface under the vehicle;
    detecting the light of at least one wavelength reflected by the roadway surface;
    acquiring at least one information item relating to a condition of the roadway surface based on the detected reflected light;
    transmitting the at least one information item to the at least one driver assistance system; and
    modifying a time for intervention y the stability adjuster based on a comparison of a required coefficient of friction with a coefficient of friction between wheels of the vehicle and the roadway surface estimated using the condition of the roadway surface, the required coefficient of friction being determined from the vehicle's velocity and steering wheel lock for cornering.

2. The method as claimed in claim 1, wherein the at least one information item comprises information representative of whether the roadway surface is at least one of wet, icy, snow-covered and dry.

3. The method as claimed in claim 1, wherein the at least one information item comprises information representative of whether the roadway surface includes concrete or asphalt.

4. The method as claimed in claim 1, wherein the at least one driver assistance system further comprises an anti-lock brake system.

5. The method as claimed in claim 4, wherein the modifying further comprises setting a first control cycle of the anti-lock brake system as a function of the condition of the roadway surface.

6. The method as claimed in claim 1, wherein the at least one driver assistance system further comprises, a transmission controller of an automatic transmission.

7. The method as claimed in claim 6, wherein the modifying further comprises setting at least one of a shift time and a gear speed to be engaged of the automatic transmission as a function of the condition of the roadway surface.

8. The Method as claimed in claim 1, wherein the at least one driver assistance system further comprises an offroad mode.

9. The method as claimed in claim 8, wherein the modifying further comprises setting the offroad mode as a function of the condition of the roadway surface.

10. The method as claimed in claim 1, wherein the light of the at least one wavelength comprises light of three different wavelengths in the infrared range.

11. The method as claimed in claim 1, wherein detecting the light of at least one wavelength reflected by the roadway surface comprises detecting diffusely reflected light and light that is reflected in a mirroring fashion.

12. The method of claim 1, wherein the emitting comprises emitting the light onto the roadway surface under the vehicle at a substantially vertical direction.

13. A device for controlling at least one driver assistance system of a vehicle, the at least one driver assistance system comprising a stability adjuster, the device comprising:
   an optical surface sensor configured to acquire at least one information item relating to the condition of a roadway surface; and
   a controller connected to the optical surface sensor and to the at least one driver assistance system, the controller being configured to modify a time for intervention by the stability adjuster based on a comparison of a required coefficient of friction with a coefficient of friction between wheels of the vehicle and the roadway surface estimated using the condition of the roadway surface, the required coefficient of friction being determined from the vehicle's velocity and steering wheel lock for cornering.

14. The device as claimed in claim 13, wherein the at least one information item comprises information representative of whether the roadway surface is at least one of wet, icy, snow-covered and dry.

15. The device as claimed in claim 13, wherein the at least one information item comprises information representative of whether the roadway surface includes concrete or asphalt.

16. The device as claimed in claim 13, wherein the at least one driver assistance system further comprises an anti-lock brake system.

17. The device as claimed in claim 16, wherein the modifying further comprises setting a first control cycle of the anti-lock brake system such that the anti-lock brake system operates as a function of the condition of the roadway surface.

18. The device as claimed in claim 13, wherein the at least one driver assistance system further comprises a transmission controller of an automatic transmission.

19. The device as claimed in claim 13, wherein the at least one driver assistance system further comprises an offroad mode.

20. The device as claimed in claim 13, wherein the optical surface sensor comprises:
   a light source unit configured to emit light of at least one wavelength onto the underlying surface; and
   at least a first detector configured to detect the light reflected by the roadway surface.

21. The device as claimed in claim 20, wherein the light source unit and the at least one detector are disposed in a housing.

22. The device as claimed in claim 20 further comprising at least a second detector configured to detect light reflected in a mirroring fashion.

23. The device as claimed in claim 20, wherein the light source unit comprises three light sources, each of the three light sources being configured to emit light at a different wavelength.

24. A vehicle comprising the device as claimed in claim 13.

* * * * *

UNITED STATES PATENT AND TRADEMARK OFFICE
CERTIFICATE OF CORRECTION

PATENT NO.         : 9,135,219 B2                                    Page 1 of 1
APPLICATION NO.    : 13/807368
DATED              : September 15, 2015
INVENTOR(S)        : Hartmut Binder et al.

It is certified that error appears in the above-identified patent and that said Letters Patent is hereby corrected as shown below:

Claims

Column 12, line 64, Claim 1, delete "y", and insert -- by --.

Signed and Sealed this
Second Day of February, 2016

Michelle K. Lee
*Director of the United States Patent and Trademark Office*